United States Patent [19]

Holtkamp, Sr.

[11] Patent Number: Plant 7,104

[45] Date of Patent: Jan. 9, 1990

[54] AFRICAN VIOLET PLANT NAMED IRENE

[76] Inventor: Reinhold Holtkamp, Sr., Werther Strasse 112, D4294 Isselburg, Fed. Rep. of Germany

[21] Appl. No.: 310,630

[22] Filed: Feb. 15, 1989

[51] Int. Cl.[4] ..... A01H 5/00
[52] U.S. Cl. ..... Plt./69
[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Irene characterized by its wavy, semi-double, variegated blue and white flowers with frilled edges; strong, upright flower stems that curve sligthly toward the center to form a compact bouquet above the leaves; medium green, round, slightly serrated leaves; profuse flowering, vigorous and compact growth habit, flowering 10–11 weeks after potting, and its long lasting and non-dropping flowers.

1 Drawing Sheet

1

The present invention comprises a new and distinct cultivar of African violet plant, botanically known as *Saintpaulia ionantha,* and hereinafter referred to by the cultivar name Irene.

The new cultivar was referred to during the breeding and selection process by the designation 6 F 30/16 bl. we. and is a product of a planned breeding program. The new cultivar was originated from a cross made by me in the controlled breeding program in Haffen, Federal Republic of Germany. The female, or seed parent was a cultivar designated 43/2. The male, or pollen parent was a cultivar designated 30/16 bl.

Irene was discoverd and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar was firmly fixed and retained through successive generations of asexual reproduction.

Irene has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Irene, which in combination distinguish this African violet as a new and distinct cultivar:

(1) Strong, upright flower stems curving slightly toward the center.

(2) Semi-double, wavy, white and blue variegated flowers with frilled edges.

(3) Profuse flowering.

(4) Each plant carries 10–12 and more upright flower stems each of which carries 6–8 and more flowers.

(5) Long lasting, non-dropping flowers.

(6) Vigorous and compact grower.

(7) Plant saleable 10 to 11 weeks after potting.

(8) Seed capsules push slightly through.

(9) Medium green, round leaves, slightly serrated.

2

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 1 p.m. in Nashville, Tenn.

Botanical classification: *Saintpaulia ionantha,* Ramat., c.v. Irene.

Parentage:

*Male parent.*—30/16 bl.

*Female parent.*—43/2.

Propagation: The new cultivar holds its distinguishing characteristics through successive propagations by leaf cuttings.

Plant. From 9 cm to 12 cm tall when grown in pots, and approximately 24–27 cm in diameter when fully grown.

*Leaves.—General form: Round. Diameter:* 60–65 mm. Texture: Leatherlike. Aspect: Shiny, hairy, slightly serrated. Veins: Upperside: visible; underside: well pronounced, light green, shiny. Color (upperside): Yellow-Green Group 147 A. Color (underside): Greyed-Green Group 194 D. Petiole: Strong upright, light green, hairy.

*Flowers.*—Buds: Bell-shaped, 6–7 mm just before opening. Sepals: Five (5). Color: Light green with brownish touch. Calyx: Shape: Funnel-shaped. Aspect: Spear-shaped, hairy. Peduncle: Character: Strong upright, hairy. Color: Light green, occasionally brownish touch. Individual flowers: Size: 35–40 mm. Shape: Semi-double (4–5 additional small petals), wavy with frilled edges. Color (upperside): Variegated white and Violet-Blue Group 93 C to D. Under cooler temperatures and more intensive lighting, the blue tends to intensify. Color (underside): Variegated white and Violet-Blue Group 93 C to D. Borne: Each flower stem carries 6–8 and more flowers on strong, upright peduncle that are free standing above the leaves, thereby forming a compact bouquet. Flowering habit: Flowers 10–11 weeks after potting.

*Reproductive organs.*—Stamens: Two (2). Anthers: 2 composed of 4 anther cells, seed capsules push slightly through. Filaments: Yellowish green, 4 mm long. Pollen color: Yellow Group 7 A. Styles: 6 mm long, purplish blue, base of ovary light green and hairy.

*Roots.*—Normally developed, white when young, turning slightly brownish when older.

Disease resistance: Good.

General Observations: Irene has an extremely attractive appearance due to its variegated blue and white flowers. The flowers are semi-double, having 4–5 additional small petals, wavy and frilled at the edges. The blue color radiates somewhat from the center into the petals and varies from 1–5 mm on the edges. A tight bouquet of flowers free standing above the leaves develops after approximately 10–11 weeks. Each of the 10–12 and more strong flower stems carries 6–8 and more flowers which are long-lasting and non-dropping. The medium green, round, slightly serrated leaves give the plant a fresh look. The seed capsules push slightly through.

I claim:

1. A new and distinct cultivar of African violet named Irene, as described and illustrated, and particularly characterized by its wavy, semi-double, variegated blue and white flowers with frilled edges; strong, upright flower stems that curve slightly toward the center to form a compact bouquet above the leaves; medium green, round, slightly serrated leaves; profuse flowering, vigorous and compact growth habit, flowering 10–11 weeks after potting, and its long lasting and non-dropping flowers.

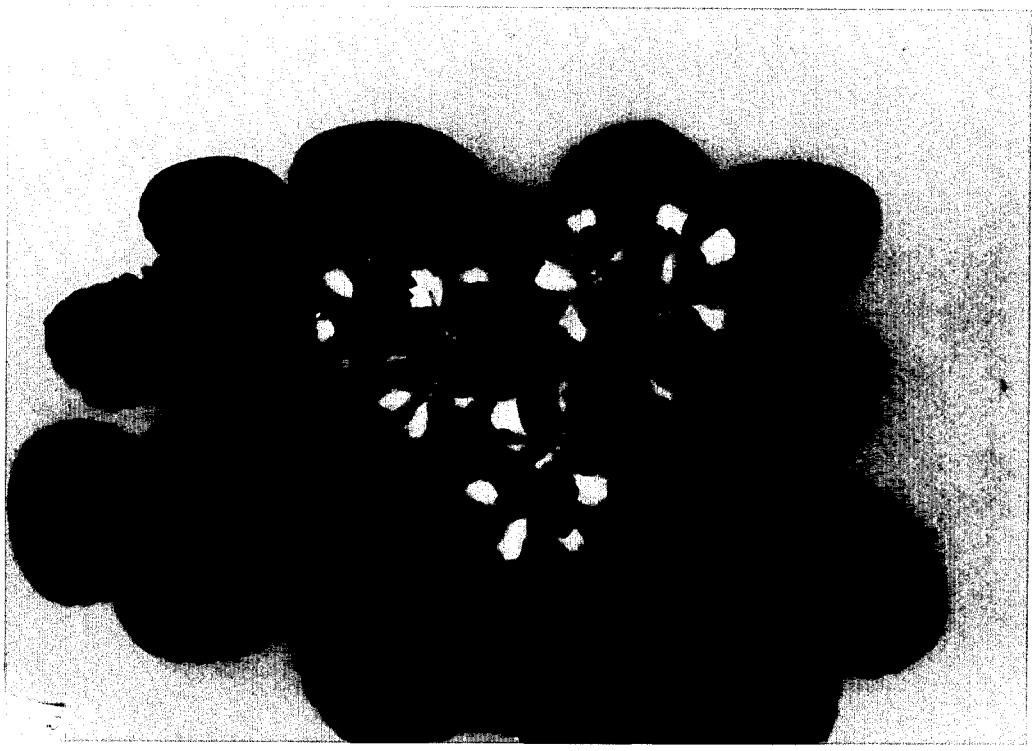

* * * * *